(12) United States Patent
Jewell et al.

(10) Patent No.: US 8,037,546 B2
(45) Date of Patent: Oct. 18, 2011

(54) ATHLETIC PANTS WITH INTEGRAL KNEE SUPPORT

(76) Inventors: Gayle L. D. Jewell, Richmond Hill (CA); Russell G. Kitteringham, Richmond Hill (CA)

( * ) Notice: Subject to any disclaimer, the term of this patent is extended or adjusted under 35 U.S.C. 154(b) by 289 days.

(21) Appl. No.: 12/349,862

(22) Filed: Jan. 7, 2009

(65) Prior Publication Data

US 2009/0144873 A1 Jun. 11, 2009

Related U.S. Application Data

(63) Continuation-in-part of application No. 11/153,527, filed on Jun. 15, 2005, now Pat. No. 7,496,973.

(51) Int. Cl.
*A41D 13/00* (2006.01)

(52) U.S. Cl. .......................................................... 2/227

(58) Field of Classification Search .............. 2/227, 228, 2/16, 79, 69, 456, 911, 22, 24; 128/878, 128/881, 882; 602/16, 26, 62
See application file for complete search history.

(56) References Cited

U.S. PATENT DOCUMENTS

| | | | |
|---|---|---|---|
| 1,698,012 A | 1/1929 | Cruden | |
| 3,786,804 A * | 1/1974 | Lewis | 602/16 |
| 3,900,898 A * | 8/1975 | Ackerman | 2/22 |
| 4,064,874 A * | 12/1977 | Valin | 602/26 |
| 4,156,294 A * | 5/1979 | Horn | 2/400 |
| 4,811,427 A * | 3/1989 | Regan | 2/466 |
| 4,850,056 A * | 7/1989 | Gardner et al. | 2/227 |
| 5,139,477 A * | 8/1992 | Peters | 602/26 |
| 5,539,926 A | 7/1996 | Mantos | |
| 6,023,789 A * | 2/2000 | Wilson et al. | 2/228 |
| 6,231,488 B1 * | 5/2001 | Dicker et al. | 482/124 |
| 6,701,533 B2 * | 3/2004 | Webb | 2/303 |
| 6,782,559 B2 * | 8/2004 | Regan | 2/455 |
| 7,237,270 B2 * | 7/2007 | Crye et al. | 2/24 |

* cited by examiner

*Primary Examiner* — Tejash Patel
(74) *Attorney, Agent, or Firm* — Sand & Sebolt

(57) ABSTRACT

An athletic pant that includes an area of compressive fabric disposed in a position on either pant leg that will surround the athlete's knee when the pants are worn. The area of compressive fabric in each pant leg also includes a pair of pockets positioned to lie on either side of the athlete's knee. The pockets completely enclose a support that aids in restricting lateral movement of the athlete's knee. The athletic pants may extend to the athlete's mid-calf region or to the ankle. The pants further include at least one cinch strap that is operable to reduce the diameter of the pant legs in the vicinity of the athlete's knee, thereby improving the fit of the pant for the athlete.

30 Claims, 7 Drawing Sheets

ATHLETIC PANTS WITH INTEGRAL KNEE SUPPORT

CROSS-REFERENCE TO RELATED APPLICATIONS

This is a Continuation-in-Part of U.S. patent application Ser. No. 11/153,527, filed Jun. 15, 2005, the entire specification of which is incorporated herein by reference.

BACKGROUND OF THE INVENTION

1. Technical Field

This invention generally relates to athletic apparel. More particularly, the invention relates to athletic pants. Specifically, the invention relates to a pair of pants having a compressive, elastic region disposed to surround the athlete's knee, said region including a pair of pockets positionable on either side of the knee, each pocket completely enclosing a reinforcing support therein. The pants may further include cinching straps that permit the athlete to reduce the diameter of the elastic region of the pant leg in the vicinity of the knee.

2. Background Information

It is fairly common for athletes to sustain injuries to their knees during practice sessions or games. In many instances, the athlete has to use a support of some type to protect their knees in order to prevent further injury or to hold their knee in a particular position to reduce pain. Many supports and brace type devices have been disclosed in the prior art for protecting and supporting knees. These devices include tensor bandages, elastic knee braces, and knee supports that include plastic strips or rigid, hinged aluminum strips to keep the knee in a certain position. Some of these support devices are simply pulled over the athlete's foot and raised up to their knee and the elasticity of the device holds it in place. Most of these appliances, however, are positioned proximate the athlete's knee with a series of straps. The appliances need to be positioned accurately to ensure proper limitation of the movement of the knee.

The prior art appliances work fairly well until they come into contact with clothing such as football or baseball pants that end at or below the knee. As these pants move up and down in response to movement by the athlete, they tend to rub against the knee supporting appliance and push or pull the support out of the optimum position. This may not only prevent the appliance from protecting the athlete's knee but can also result in the athlete's play being impeded because the appliance gets in the way.

This problem has been partially addressed in the prior art, such as in the device proposed in U.S. Pat. No. 4,850,056, issued to Gardner et al. Gardner et al discloses a pair of athletic pants that are designed to be worn over a knee supporting device such as a device that is secured to the athlete's leg by straps wrapped around the thigh and calf. Gardner's athletic pants include a flap sewn onto the inner surface of the pant leg at a position that would fall slightly above the athlete's knee. The thigh strap of the supporting device can be releasably connected to this flap to reduce the tendency of the supporting device to slide down the athlete's leg in response to movements of the pants. Gardner et al's pants may help in keeping the knee supporting device in a slightly better position that if there was no connection between the pants and supporting device, but the athlete has to secure the knee supporting device to their knee, pull the pant leg over the device and then secure the device to the flap. During the step of puling the pant leg over the device, the device can be shifted out of optimum position. Furthermore, the positioning of the flap and the strap of the device can be slightly off, resulting in the device being shifted by the flap when the athlete next moves.

There is therefore a need in the art for an improved device for supporting the knee of an athlete that allows for correct positioning of the support around the knee and that is easier to put on and maintain in the correct position.

SUMMARY OF THE INVENTION

The device of the present invention comprises an athletic pant that includes an area of compressive fabric disposed in a position on either pant leg that will surround the athlete's knee when the pants are worn. The area of compressive fabric in each pant leg also includes a pair of pockets positioned to lie on either side of the athlete's knee. The pockets completely enclose a support that aids in restricting lateral movement of the athlete's knee. The athletic pants may extend to the athlete's mid-calf region or to the ankle. The pants further include at least one cinch strap that is operable to reduce the diameter of the pant legs in the vicinity of the athlete's knee, thereby correcting or adjusting the fit of the pant for the user.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

FIG. 5a is a top view of the arcuately-shaped support that is receivable within the pocket of the pants of FIG. 5;

DETAILED DESCRIPTION OF THE INVENTION

Figure 1:
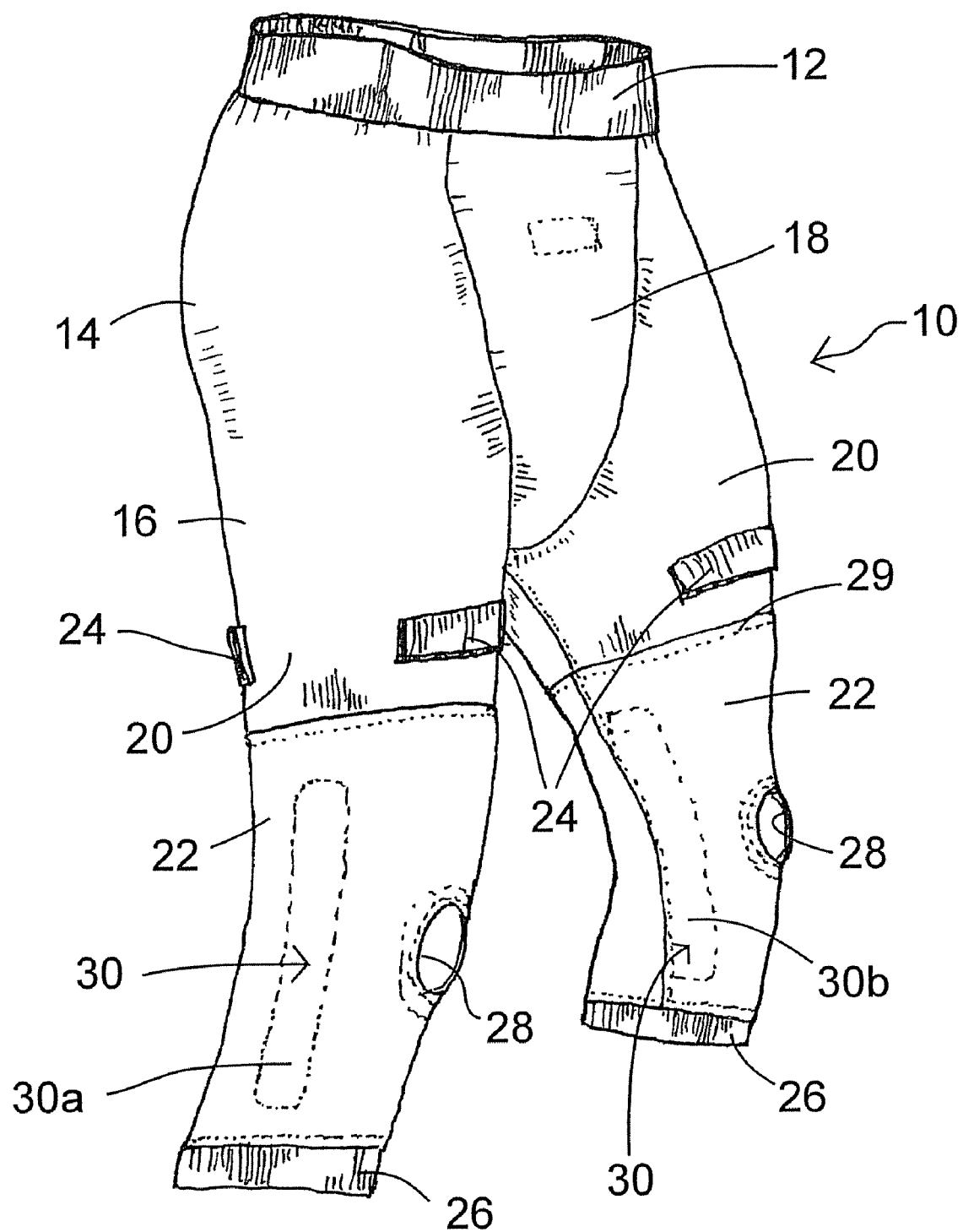
FIG. 1 is a perspective view of a first embodiment of athletic pants in accordance with the present invention.
Figure 2:
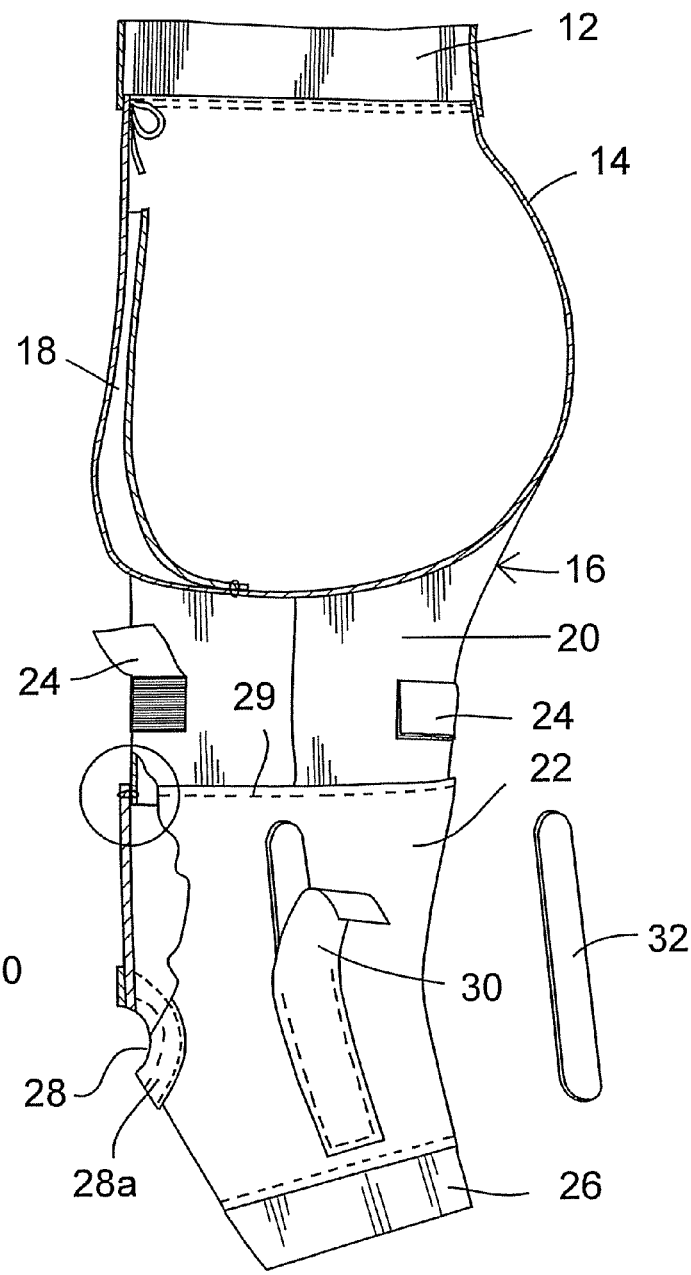
FIG. 2 is a partial cross-sectional side view of the athletic pants of FIG. 1 and showing the support removed from the pocket.

Referring to FIGS. 1&2, there is shown a pair of athletic pants in accordance with the present invention and generally indicated at 10. Pants 10 include an elastic waistband 12, a body 14 and two pant legs 16 extending outwardly from body 14. Body 14 encompasses the abdomen and buttocks of the player and may include pockets 18 for holding protective equipment such as cups or pads (not shown).

Each leg 16 of pants 10 includes a first region 20 designed to encompass the upper portion of an athlete's thigh and a second region 22 designed to encompass the lower portion of the athlete's thigh, their knee and the upper portion of their calf. First region 20 is integrally formed with body 14 and preferably is manufactured from the same fabric. The fabric selected for first region 20 depends on the type of sport that the pants 10 are used for. The athletic pants 10 shown in FIGS. 1&2 are used in playing ice hockey. First region 20 is consequently manufactured from a fabric such as spandex and nylon. Ice hockey players wear long socks (not shown) that are held up by a suitable means such as a strap secured around the player's thigh or by hook and pile fasteners positioned on another garment. Athletic pants 10 in accordance with the present invention include a plurality of strips 24 of hook and pile fasteners positioned at intervals on first region 20 of pant legs 16. As will be later described, the long socks are pulled up over pants 10 and the top of the socks are secured to strips 24.

In accordance with one of the specific features of the present invention, second region 22 extends outwardly away from first region 20. Second region 22 is manufactured from a stretchy, elastic material that preferably places those parts of the leg it covers under compression. Second region 22 is therefore adapted to fit tightly around the lower thigh, knee and upper calf of the player. In the case of athletic pants for ice hockey players, second region 22 preferably is manufactured from a material such as neoprene rubber. An elastic cuff 26 is provided at the end of second region 22 to assist in keeping the second region from riding up the athlete's leg. Second region 22 also includes an aperture 28 which is positioned to align with the athlete's kneecap (not shown) and which allows second region 22 to be bent in a manner that substantially prevents the cuff 26 from riding up on the athlete's leg. A reinforced area 28a is provided immediately surrounding aperture 28. Reinforced area 28a serves to apply pressure to prevent second region 22 from tearing or shifting during movement of the athlete's leg.

In accordance with another specific feature of the present invention, second region 22 is provided with a pair of pockets 30a, 30b which each receive a support 32 therein. The pockets 30a, 30b are positioned one on either side of aperture 28. Each pants leg 16 has a longitudinal axis that runs from waistband 12 through to the bottom 26 of second region 22. Pockets 30a, 30b are oriented substantially parallel to the longitudinal axis of their respective pant leg 16. Pockets 30a, 30b may be formed by securing a segment of material over second region 22 by way of stitches and/or a hook and pile fastener material such as that sold under the Velcro® trademark. (Velcro® is a registered trademark of Velcro Industries B.V. of the Netherlands.) Supports 32 are planar or hinged members manufactured from plastic, aluminum or any other suitable material that is rigid and will therefore provide lateral support for the athlete's knee. Pockets 30a, 30b are partially stitched to second region 22 and include a section that is closed by way of hook and pile fasteners. This allows supports 32 to be inserted into pockets 30a, 30b and to be retained therein. Supports 32 may be removed from pockets 30a, 30b when athletic pants 10 are washed or if a support 32 breaks and needs to be replaced.

Figure 3A:
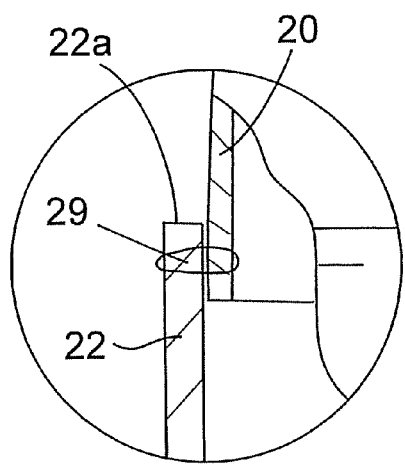
FIG. 3a is an enlarged cross-sectional side view of the circled area of FIG. 2 showing a permanent connection of the stretchy fabric to the athletic pants.
Figure 3B:
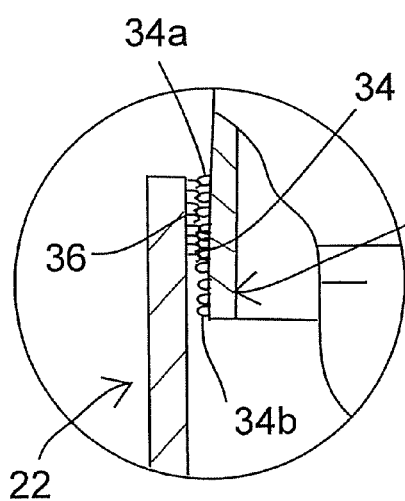
FIG. 3b is an enlarged cross-sectional side view of the circled area of FIG. 2 showing a first mechanism for adjusting the position of the stretchy fabric on the athletic pants and to thereby adjust the relative position of the stretchy fabric on an athlete's leg.

As can be seen in FIGS. 3a and 3b, first and second regions 20, 22 may be connected together in different ways. FIG. 3a illustrates the instance where first and second regions 20, 22 are permanently sewn together and therefore the aperture 28 for the patella (knee-cap) is preset a certain distance from waistband 12. First and second regions 20, 22 are sewn together with first region 20 positioned inwardly of second region 22 so that second region 22 overlaps first region 20. This arrangement is preferred as the athlete's foot will not become snagged on the end 22a of second region 22 when the pants 10 are pulled on. It will, however, be understood that second region 22 may alternatively be placed on the inside of first region 20, without departing from the spirit of the present invention. Furthermore, it will be understood that any other type of seam may be utilized to connect the first and second regions together without departing from the present invention.

FIG. 3b shows an arrangement for connecting the first and second regions 20, 22 together in a manner that allows the distance between waistband 12 and aperture 28 to be adjusted for an improved fit. In this second instance, one of first and second regions 20, 22 is provided with a circumferential band 34 of hook-type fasteners and the other of the first and second regions 20, 22 is provided with a circumferential band 36 of pile-type fasteners. The athlete can therefore adjust the position of the second region 22 relative to the first region 20 by increasing or decreasing the distance between waistband 12 and first and second regions 20, 22. So, if the athlete has a shorter thigh, fasteners 36 on second region 22 are positioned proximate the upper edge 34a of the band of fasteners 34 on first region 20 (FIG. 3b). If the athlete has a longer thigh, the band of fasteners 36 on second region 22 is positioned proximate the bottom edge 34b of the band of fasteners 34 (not shown). This adjustability allows the athlete to place the supports 32 at the correct position along either side of their knee.

Athletic pants 10 are used in the following manner. The athlete (not shown) inserts his feet through an aperture (not shown) that is surrounded by cuff 26. He draws the pants upwardly until waistband 12 is comfortably seated around his waist. He manipulates second region 22 so that his knee-cap protrudes through aperture 28. At this point, the upper portion of each of the athlete's thighs are covered by first region 20 and the lower portion of his thighs are covered by that part of second region 22 that lies between aperture 28 and the seam 29 between first and second regions 20, 22. Furthermore, the upper portion of each calf is covered by that part of second region 22 that lies between aperture 28 and cuff 26. Pockets 30a and 30b in each pant leg 16 are positioned on either side of the athlete's knee and supports 32 in each of the pockets 30a, 30b are disposed so as to substantially prevent lateral movement of the knee. The athlete who, for the purposes of this description, is an ice hockey player, pulls on each of his hockey socks (not shown) and draws the upper end of each sock upwardly toward his waist until the upper end can engage with the Velcro® strips 24 and be locked in place. He can then pull on his shorts over pants 10 and engaged hockey socks, will put on his ice skates (not shown) and be ready to play. If it is found that support 32 is broken or needs to be removed for some other reason, the athlete can simply disengage the upper end of his hockey socks from strips 24, pull the sock down and open the Velcro® fasteners on pocket 30a, for example, and gain access to support 32 inside that pocket. When he is finished adjusting or replacing support 32, pocket 30a may be closed again by closing the Velcro® fasteners, thereby securing support 32 in pocket 30a. The hockey socks can be pulled up again and be reengaged with strips 24. It will be understood that the supports 32 can be placed in pockets 30a, 30b prior to the athlete putting the pants 10 on or, alternatively, supports 32 can be placed in pockets 30a and 30b after the athlete has already pulled pants 10 on. It will also be understood that supports 32 can be removed from pockets 30a, 30b whether pants 10 are on the athlete or off the athlete.

Referring to FIG. 3b, athletic pants 10 that include this form of attachment between first region 20 and second region 22 can be adjusted to ensure that aperture 28 is correctly aligned with the athlete's knee-cap. This adjustment can be made before pants 10 are put on or after pants 10 are put on. In order to make the adjustment, the athlete pulls the hook and pile fasteners out of engagement with each other and then adjusts the relative position of the bands 34 and 36 relative to each other. If the athlete wants to shorten the distance between waistband 12 and aperture 28, then band 36 is positioned proximate the upper end 34a of band 34. If the athlete wants to lengthen the distance between waistband 12 and aperture 28, then band 36 is positioned proximate the bottom end 34b of band 34. Once the bands 34, 36 are placed in the desired position relative to each other, the hook and pile fasteners in bands 34, 36 are pushed back into contact with each other, thereby securing first and second regions 20, 22 together.

Figure 4:
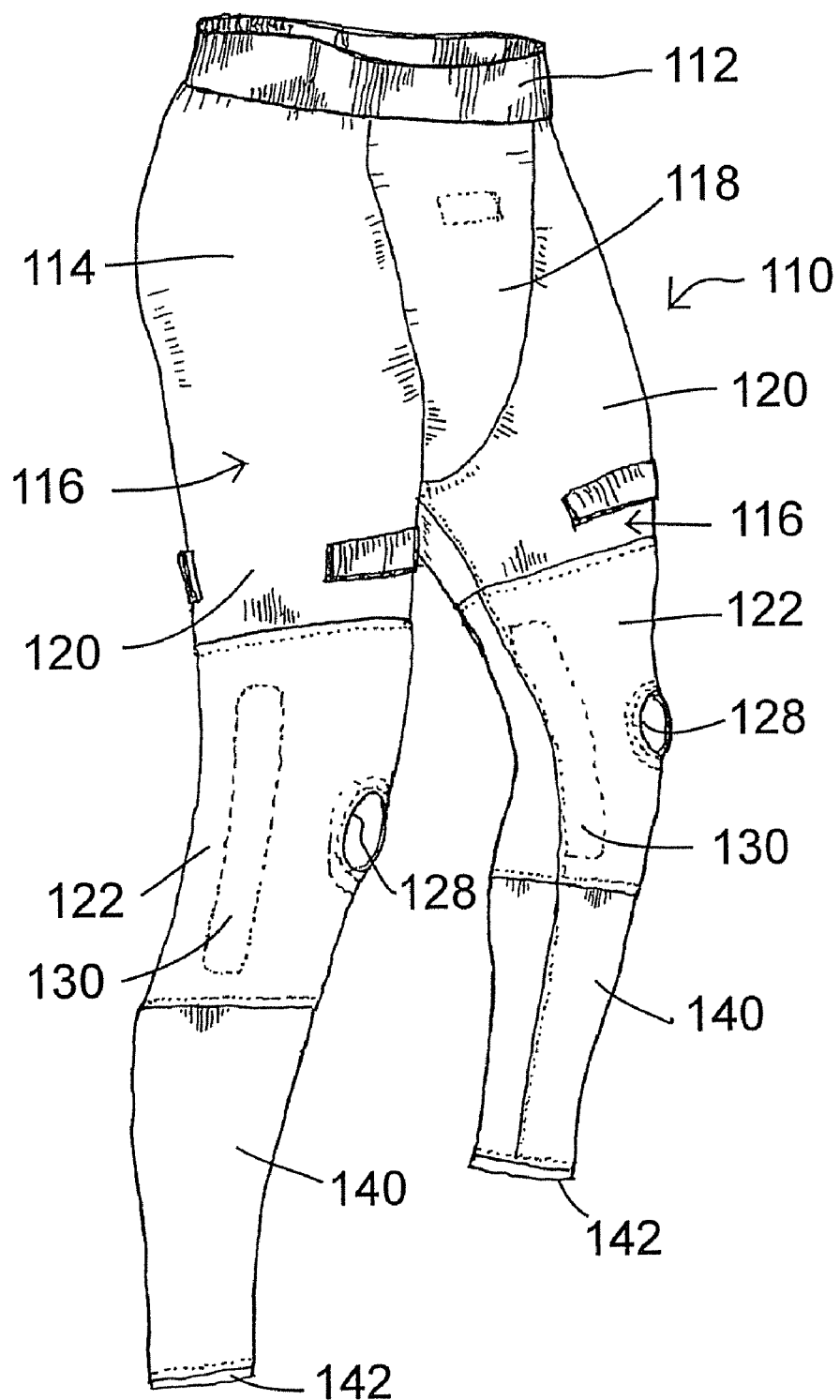
FIG. 4 is a perspective view of a second embodiment of the athletic pants in accordance with the present invention and showing a third region that is designed to cover the athlete's calf from a region proximate the knee to a region proximate the ankle.

Referring to FIG. 4, there is shown a second embodiment of athletic pants in accordance with the present invention and generally indicated at 110. As with the first embodiment, athletic pants 110 include an elastic waistband 112, a body 114 and pant legs 116 extending outwardly from body 114. A pocket 118 is formed on body 114 for receiving protective equipment such as a cup (not shown). Pant legs 116 comprise a first region 120, a second region 122 and a third region 140. First region 120 preferably is sewn to second region 122 and second region 122 preferably is sewn to third region 140. Third region 140 is adapted to extend to the ankles of the athlete and consequently tapers from its attachment to second region 122 down to the end 142. End 142 may comprise an elastic cuff. First and third regions 120, 140 preferably are made from the same material, with second region 122, being made from a different material, namely a stretchy, elastic fabric such as neoprene rubber that compresses the parts of the body that it contacts. All of the components of the second region 122 are substantially identical to the components of that region in athletic pants 10. It will be understood that while the above description indicates that the first, second and third regions 120, 122 and 140 are sewn together, the first and second regions 120, 122 may be joined together by circumferential bands of mating hook and pile fasteners. This type of attachment would ensure that the position of the second region 122 is adjustable.

Athletic pants 110 are used in the same manner as athletic pants 10, except the athlete inserts his foot through an aperture (not shown) in proximate the bottom 142 of third region 140. The bottom 142 of third region 140 is adapted to encircle the athlete's ankle. Once the waistband 112 surrounds the athlete's waist, he then adjusts the position of second region 122 until his knee-cap is positioned behind aperture 128 and pockets lie on either side of his knee. The athlete can then pull on his hockey socks and connect them to pants 110 in the manner described with respect to the previous embodiment of the invention.

Figure 5:
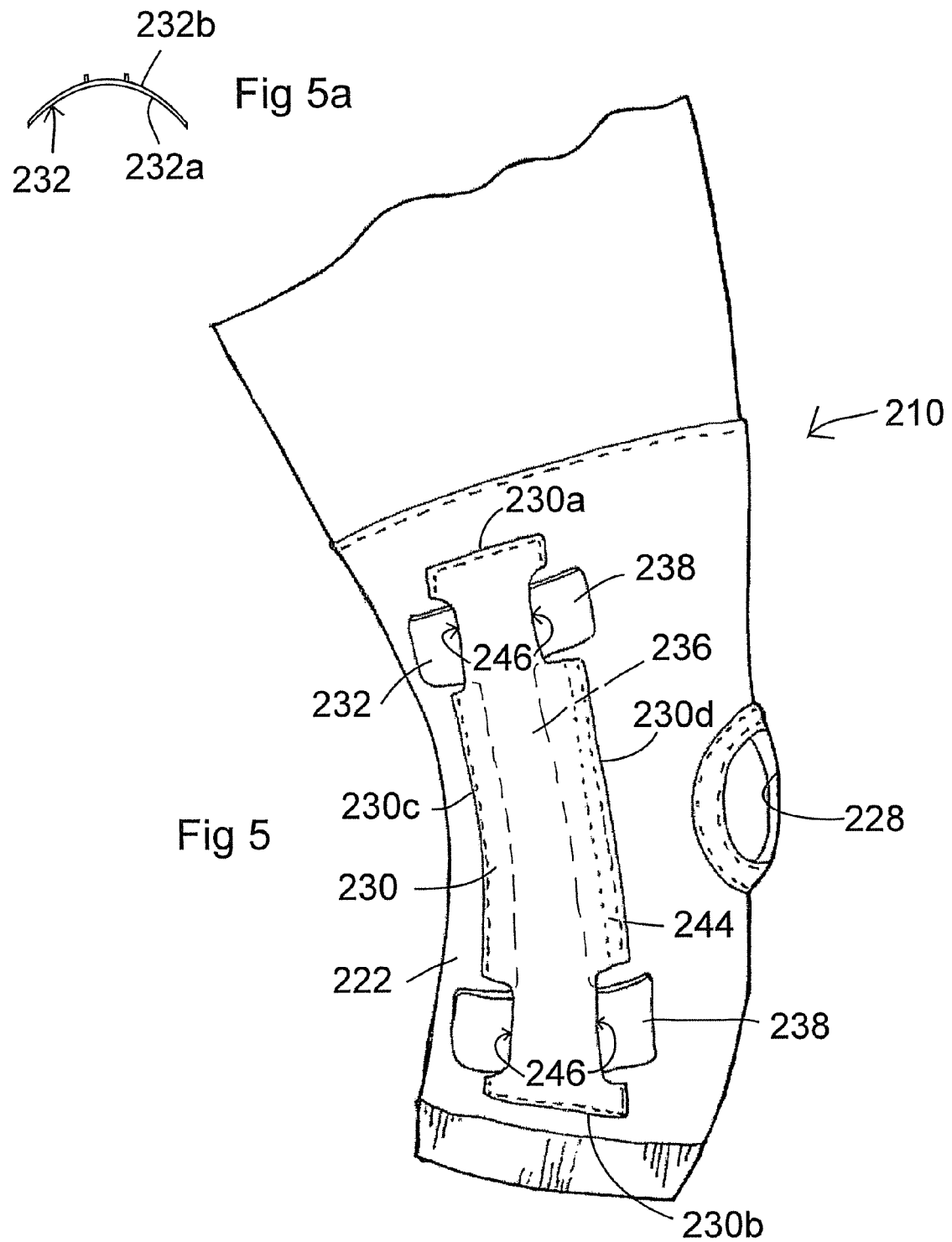
FIG. 5 is a partial perspective view of a third embodiment of athletic pants in accordance with the present invention, where the pants include a pocket for receiving a support that is arcuate in shape.

A third embodiment of athletic pants in accordance with the present invention is shown in FIGS. 5 & 5a and is generally indicated at 210. The structure of pants 210 is substantially identical to the structure of pants 10 except for the pocket 230 provided for holding a support 232. Support 232 is substantially I-shaped comprising a central portion 236 with flexible upper and lower arms 238 lying substantially at right angles thereto. Pocket 230 is generally I-shaped and is sewn onto second region 222 along a top edge 230a, a bottom edge 230b and a first side 230c. The opposite side 230d is secured to second region 222 by mating hook and pile fasteners 244. The central portion of pocket 230 includes a wider region flanked by two narrower regions. The narrower regions of pocket 230 include openings 246 through which the arms 238 of support 232 extend. Support 232 is arcuate in shape when viewed from the top or bottom (FIG. 5a) and this shape helps support 232 to be positioned on the athlete's leg and remain in place in pocket 230. The aperture 238 helps hold second region 222 centered on the athlete's knee-cap.

Athletic pants 210 are put on and pulled off in the same manner as previously described and support 232 can be inserted into pocket 230 whether pants 210 are on or off the athlete. In order to insert support 232 into pocket 230, the free edge 230d of pocket is lifted up so that hook and pile fasteners 244 disengage from each other. Support 232 is then oriented so that the interior curved surface 232a (FIG. 5a) of support 232 will abut the outer surface of second region 222 and the exterior curved surface 232b of support 232 will abut the interior surface of pocket 230. Support 232 is slid into pocket 230 so that arms 238 are received through the apertures 246 that are proximate the secured side 230c of pocket 230. Hook and pile fasteners 244 are pressed into contact with each other, thereby locking support 232 inside pocket 230. The athlete can make slight adjustments to the position of support 232 by pushing on the arms 238 of support 232 until the interior curved surface 232a hugs the athlete's leg through second region 222. The compression of second region 222 keeps support 232 properly positioned against the side of the athlete's leg.

Figure 6:
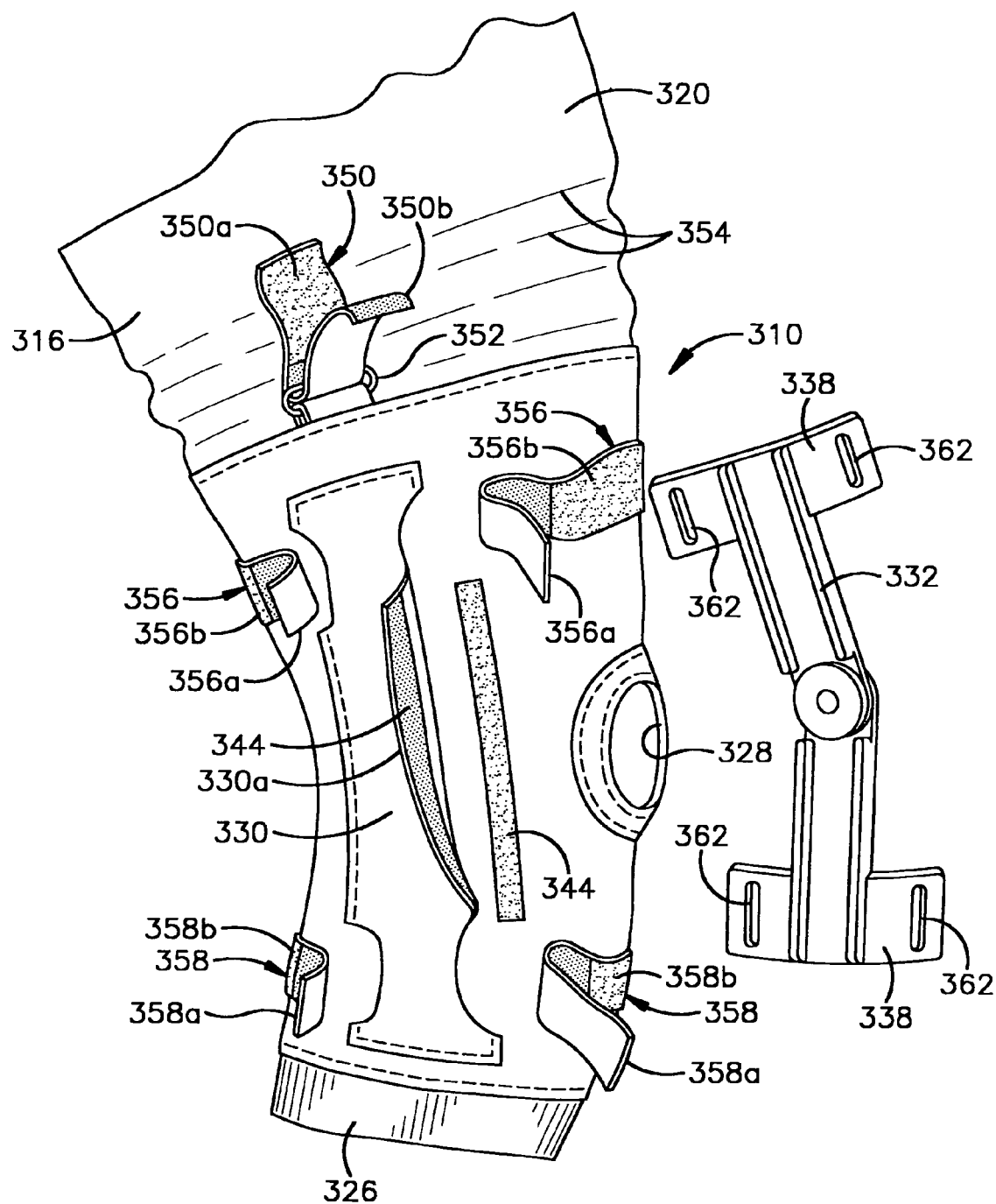
FIG. 6 is a partial perspective view of a fourth embodiment of athletic pants that includes a recloseable pocket for receiving a support, straps for aiding in holding the support in the correct position and a second mechanism for adjusting the position of the stretchy fabric on the athletic pants.

A fourth embodiment of athletic pants in accordance with the present invention is shown in FIG. 6 and is generally indicated at 310. Athletic pants 310 include a plurality of straps 350 and cooperating buckles 352 positioned at intervals on first region 320 of pants 310. A first part 350a of each strap 350 is secured to first region 320 and a second part of each strap terminates in a free end 350b that may be threaded through buckle 352. Straps 350 have hook-type fasteners at one of the secured end 350a and free end 350b and pile-type fasteners at the other of the secured end 350a and free end 350b. Upper straps 356 and lower straps 358 are provided on second region 322. Straps 356, 358 lies substantially at right angles to the longitudinal axis of pant leg 316, the longitudinal axis being defined as the direction from the waistband (not shown) to the cuff 326. Support 332 is a hinged member that includes upper and lower arms 358 which are provided with apertures 362 therein. Each of straps 356, 358 includes a section of hook fasteners and a section of pile fasteners. Straps 356, 358 are attached to the respective pant leg 316 in a manner that allows the free ends 356a, 358a of straps 356, 358 to be threaded through apertures 362 and folded back onto the fixed portion 356b, 358b of the straps. This holds supports 332 in place. Pocket 330 has substantially the same structure as pocket 230.

Athletic pants 310 are used in the following manner. As with the other embodiments of this invention, pants 310 are pulled on in a conventional manner and support 332 can be inserted into pocket 330 prior to pants 310 being pulled on or after pants 310 are pulled on. Furthermore, pants 310 can be adjusted when the pants are on or when they are off. The pants are adjusted by threading free end 350b of strap 350 through buckle 352. Free end 350b is pulled upwardly toward the waistband (not shown) and this causes the creation of gathers or folds 354 in first region 320 and causes the distance between the waistband (not shown) and aperture 338 to be reduced. (It will be understood that if the athlete desires to increase the distance between waistband and aperture 338, he pulls downwardly on second region 322 to remove some of the folds 354. When the desired distance between aperture 338 and waistband (not shown) is achieved, free end 350b of strap 350 is pushed into contact with fixed end 350a of strap 350 to allow the hook and pile fasteners thereon to engage. The athlete can consequently adjust the position of second region 322 to where the aperture 328 is correctly positioned around his knee-cap.

Support 332 is inserted into pocket 330 in the same manner as support 232 is inserted into pocket 230. Free ends 356a, 358a of each strap 356, 358 are each inserted through its respective aperture 362, the ends are pulled outwardly through apertures 362 until support 332 lies in contact with the athlete's leg, separated only by the material of second region 322. Free ends 356a, 358a are then pushed into contact with the fixed parts 356b, 358b of the straps to allow the hook and pile fasteners to engage. The free side 330a is then pushed into contact with second region 322 so that fasteners 344 engage with each other and thereby secure support 332 within pocket 330. Straps 350, 356 and 358 can be adjusted to ensure that supports 332 are held in the correct position on either side of the athlete's knee.

Figure 7:
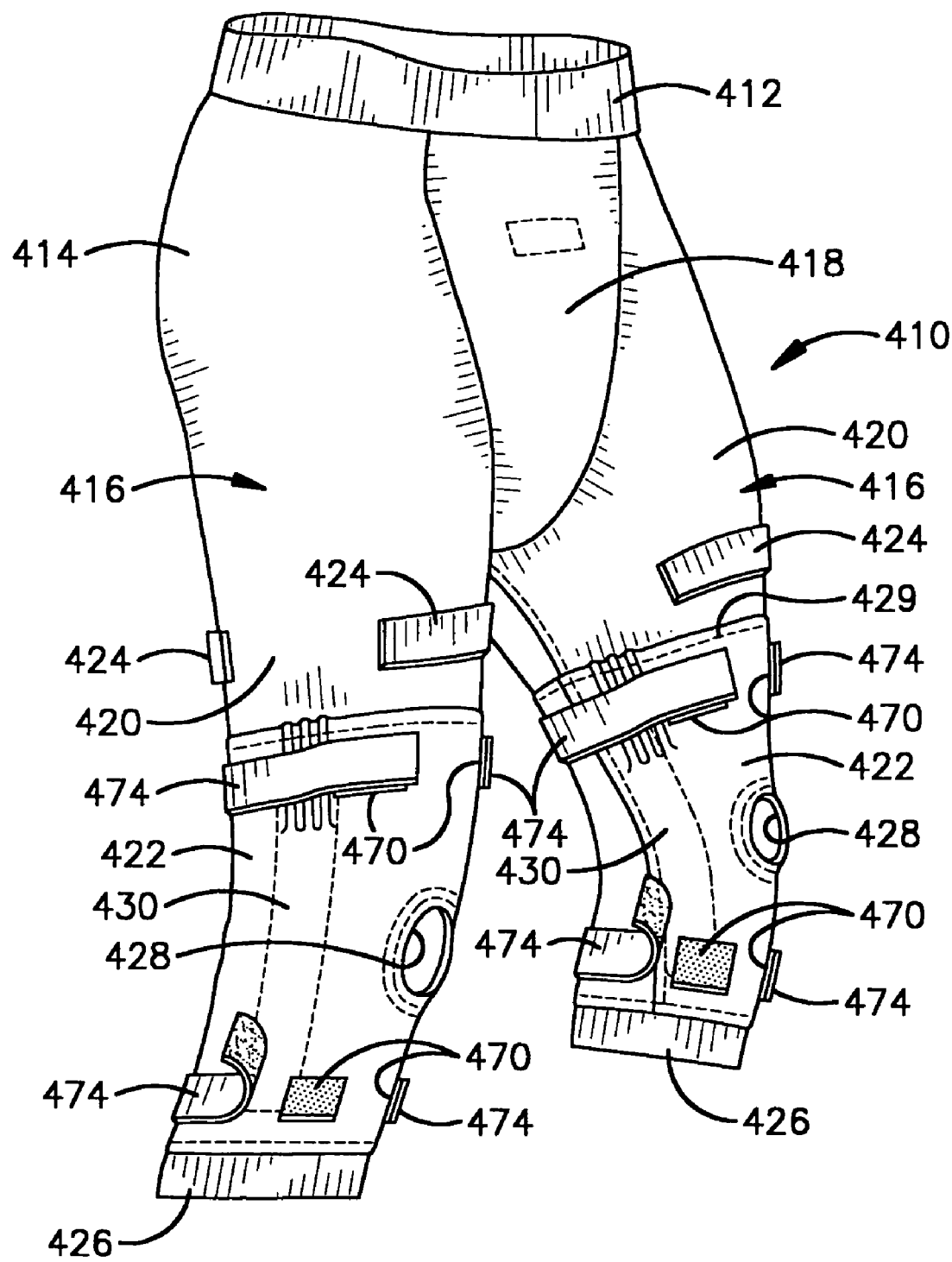
FIG. 7 is perspective view of a fifth embodiment of athletic pants in accordance with the present invention showing a pair of cinch straps proximate the top and bottom of each pocket.

Referring to FIG. 7, there is shown a fifth embodiment of the athletic pants of the present invention which are generally indicated at 410. Pants 410 are substantially identical to pants 10 shown in FIG. 1 in that they include an elastic waistband 412, a body 414 and two pant legs 416 extending outwardly from body 414. Body 414 may include pockets 418 for holding protective equipment such as cups or pads (not shown). As with the first embodiment, legs 416 have a first region 420 designed to encompass the upper portion of the athlete's thigh and a second region 422 designed to encompass the lower portion of the athlete's thigh, their knee and the upper portion of their calf. First and second regions 420, 422 are joined together along seam 429. First region 420 is integrally formed with body 414 and preferably is manufactured from the same fabric. Pants 410, as illustrated, are designed for use by ice hockey players and therefore include strips 424 of the hook and pile fastener material for securement of hockey socks thereon. It will be understood, however, that pants 410 would not include these strips 424 if the pants were designed for sports other than ice hockey. Second region 422 of pants 410 extends outwardly away from first region 420 and is manufactured from a sufficiently stretchy, elastic material that will place those parts of the athlete's leg it covers under compression. Elastic cuff 426 is provided at the lowermost end of second region 422 to assist in keeping the second region from riding up the athlete's leg. Second region 22 also defines an aperture 428 which is positioned to align with the athlete's kneecap and this aperture allows second region 422 to be bent in a manner that substantially prevents the cuff 426 from riding up on the athlete's leg. As with pants 10, the athletic pants 410 shown in FIG. 7 also include a pair of pockets 430 in second region 422 and situated on either side of aperture 428. Each pocket 430 is oriented substantially parallel to the longitudinal axis of the respective pant leg 416 and encloses a support (not shown) therein. Each pocket 430 has a front edge disposed adjacent aperture 438 and a rear edge that is disposed remote from aperture 438 and closer to a region that would fall at the back of the athlete's leg when the pants are worn. Each of the front and rear edges are disposed substantially parallel to the longitudinal axis of the pant leg. Furthermore, each pocket 430 has an upper end disposed proximate seam 429 and a lower end disposed proximate cuff 426.

In accordance with a specific feature of the present invention, pants 410 further include a plurality of cinch straps. Each cinch strap comprises a first part and a second part that are fixedly secured to the second region 422 remote from each other. Preferably, the first and second parts are laterally spaced from each other with one of the first and second parts being disposed on the pant leg in an area that will be positioned toward the front of the athlete's leg, and the other of the first and second parts being disposed in an area that will be positioned toward the back of the athlete's leg. The first and second parts preferably are horizontally aligned with each other. The first and second parts of the cinch strap are releasably and adjustably engageable with each other. When they are so engaged, an adjustable length of the fabric disposed between the first and second parts and adjacent the athlete's knee, is at least slightly gathered inwardly. The second region is thereby caused to be more closely conformed to the shape of the athlete's leg in the knee region. The cinch straps therefore effectively reduce the diameter of the pant leg in the region proximate the athlete's knee thereby correcting or adjusting the fit of the pant for the user. The degree of tightness of the pant legs is therefore controlled by the athlete themselves. It will be understood that the diameter is disposed substantially at right angles to the longitudinal axis of the pant leg 416. It should be noted that the second region of each pant leg has a circumference disposed orthogonally to the longitudinal axis of the pant leg. Furthermore, it should be noted that the cinch straps preferably do not extend around the entire circumference of the second region and the cinch straps are therefore unable to encircle the athlete's leg when the pants are worn.

In the preferred embodiment, the first part of the cinch strap comprises a connector strip 470 and the second part of the cinch strap comprises a strap member 474. Each strip 470 is secured to second region 422 in an area proximate one of the upper and lower ends of one of the pockets 430. Strips 470 are positioned in an area that will be closer to the front of the athlete's leg and preferably intermediate aperture 428 and the pocket 430. Each strip 470 preferably comprises one of a hook and pile fastener type of material.

Each strap member 474 is fixedly secured in second region 422 in an area proximate one of the upper and lower ends of pocket 430 and in a location that will be closer to the back of the athlete's leg. Each strap member 474 includes a portion that comprises the other of a hook and pile fastener material. This portion of each strap member 474 is designed to matingly engage one of strips 470.

When the athlete is wearing pants 410 he or she may decide that they would like the second region to more closely conform to the shape of their leg. In this instance, the athlete will grasp the free end of each strap member 474 and will pull it forwardly and engage the hook and pile fastener portion thereof with the associated hook and pile fastener on strip 470. This causes some of the fabric of second region 420 to become slightly gathered proximate the top and bottom ends of pocket 430. The fabric of second region 422 is slightly gathered by the tightening of these cinch straps but there is little to no effect on the fabric of first region 420.

Figure 8:
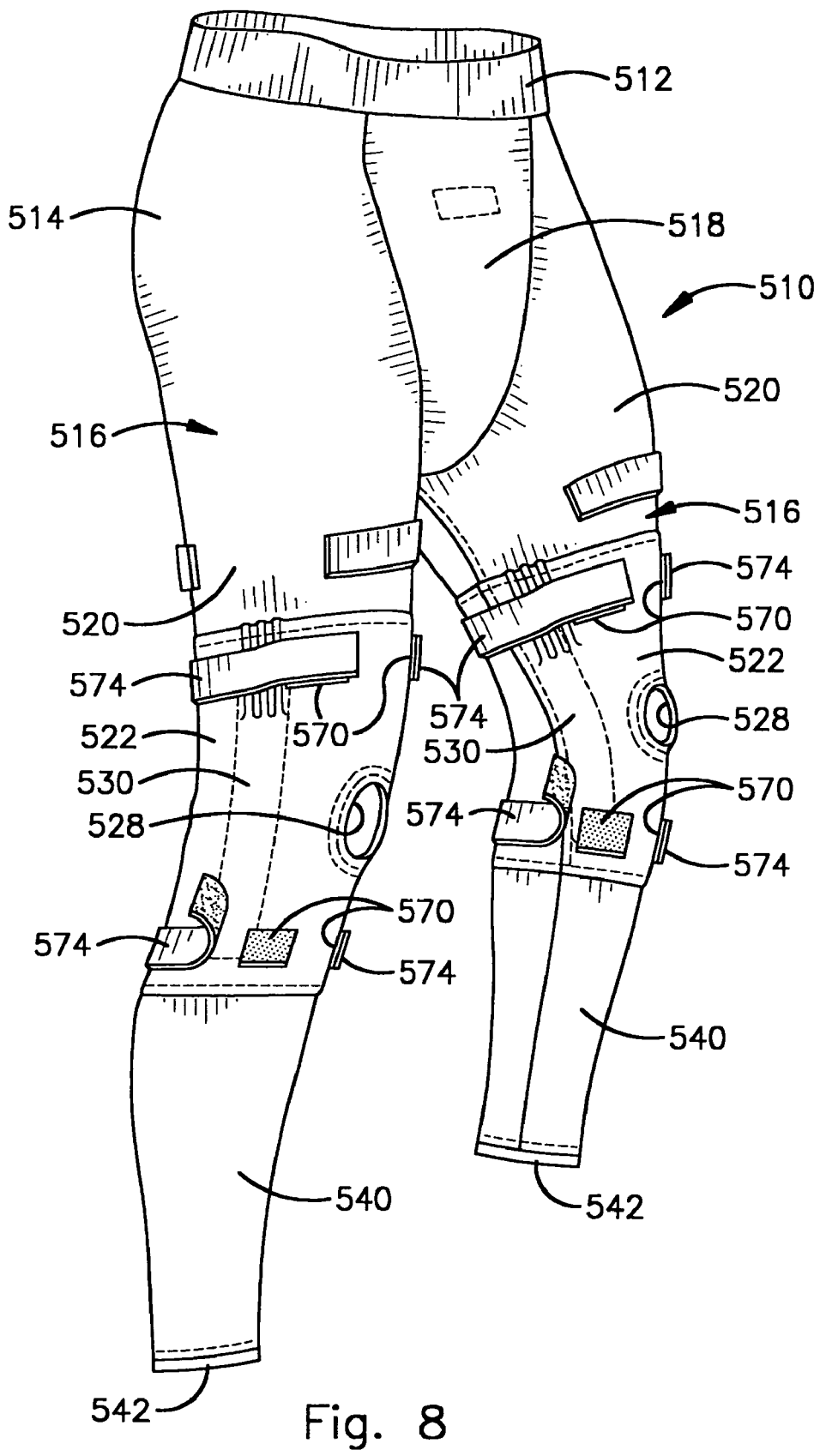
FIG. 8 is a perspective view of a sixth embodiment of the athletic pants in accordance with the present invention that includes a third region which is designed to cover the athlete's calf from a region proximate the knee to a region proximate the ankle.

FIG. 8 shows a pair of athletic pants in accordance with the present invention and generally indicated at 510. Pants 510 are substantially identical to pants 110 and include a waist band 512, body 514, pant legs 416, first, second and third regions 520, 522, 540 and cuffs 542. Pants 510 also are provided with an aperture 520 in the second regions 522 and have pockets 530 that include stiffening supports (not shown) therein. Pants 510 are shown with the strips (unnumbered) for securement of hockey socks thereon, but it will be understood that these would not be present in pants used in other applications, such as football, baseball and skiing.

In accordance with a specific feature of the present invention, pants 510 further include cinch straps that are substantially identical to those shown and described with reference to FIG. 7. Accordingly, pants 510 are provided with a plurality of strips 570 and mating strap members 574 secured proximate the top and bottom ends of pockets 530. In order to cause second regions 520 more closely conform to the athlete's legs, strap members 574 are pulled forwardly and are pressed into mating engagement with the hook and pile fastening material of strips 570. This causes the fabric of second region 522 to be slightly gathered but there is little to no effect on the fabric of first region 520 and third region 540.

It will be understood that while the cinch straps are shown as extending laterally across pockets 430, 530, they could be provided elsewhere on second regions. So, for example, one of strips 470 proximate the front of pants 410 could be replaced with a strap member 474 and likewise one of strap members 474 proximate the back of pants 410 could be replaced with a strip 470. Then, in order to gather up some of the fabric of second region 422, the strap members 474 are pulled across the front and back of the pants respectively and are engaged with the associated strip 470. Consequently, the gathered regions will be formed across the front and back of the pants and not along the sides thereof.

It will further be understood that while a pair of cinch straps is illustrated as being provided adjacent each pocket, the athletic pants could, instead, be provided with only a single cinch strap adjacent each pocket. In this instance, it would be preferable if that single cinch strap were located intermediate the upper and lower ends of the pocket.

It will be understood that while the cinch straps are shown to be comprised of a hook and pile fastener type of a strip 470 or 570 and strap member 474 or 574, the cinch straps may instead include a ring that is fixedly secured to the second region of the pants in the place of the strip 470, 570. Strap members 474, 574 could then be threaded through the ring and be doubled back on itself. Strap members 474, 574 could be secured to itself through mating regions of hook and pile fastener, snaps or a buckle type connector. Furthermore, strips 470, 570 could be positioned rearwardly of pockets 430, 530 respectively, and strap members 474, 574 could be positioned forwardly thereof. Strap members 474, 574 would then be pulled rearwardly to be matingly engaged with strips 470 or 570 respectively.

It will be understood that while the pockets on the second region have been shown as being partially sewn to second region and partially securable thereagainst by way of hook and pile fasteners, during manufacture of any of the embodiments of the athletic pants the supports can be inserted into the pockets and the pockets can be completely sewn to the second region. This would result in the support being permanently held within the pocket and not being removable therefrom.

It will also be understood that the shape of the pocket and the shape of the support are complementary, but the specific shapes of the two components can vary in accordance with the type of isolation of the knee that the pants are designed to address.

It will be further understood that the pocket preferably is made from the same material as the second region, although this is not necessary.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A pair of athletic pants for providing support to an athlete's knees, the pants comprising:
    a waistband adapted to encircle the athlete's waist;
    a body connected to the waistband and adapted to receive the athlete's abdomen and buttocks therein;
    a pair of pant legs extending outwardly from the body, the pant legs each comprising:
        a first region disposed proximate the body of the pants;
        a second region connected to the first region and being disposed remote from the body of the pants; and wherein the second region is manufactured from an elastic fabric that is able to apply a compressive force to the athlete's knee;
        a pair of pockets formed in the second region of each pant leg and positioned so as to fall on either side of the athlete's knee;
        a plurality of supporting members; each supporting member being completely enclosed within one of said pockets; and
        at least one first cinch strap provided on the second region of each pant leg, said first cinch strap being operable to reduce the diameter of the pant leg in an area proximate the athlete's knee, thereby adjusting the fit of the pant for the athlete.

2. The athletic pants as defined in claim 1, wherein each cinch strap comprises:
    a first part that is fixedly secured to the second region in a first location;
    a second part that is fixedly secured to the second region in a second location that is remote from the first location, and wherein one of said first and second parts of the cinch strap is releasably engageable with the other of the first and second parts.

3. The athletic pants as defined in claim 2, wherein each pant leg has a longitudinal axis that extends from the waistband through to an outermost end of the second region thereof; and wherein the first and second locations are spaced laterally from each other and are substantially aligned with each other in a horizontal direction orthogonal to the longitudinal axis of each pant leg.

4. The athletic pants as defined in claim 2, wherein the first location is proximate a front longitudinal edge of the pocket; and the second location is proximate a back longitudinal edge of the pocket.

5. The athletic pants as defined in claim 4, wherein both of the first and second locations are proximate an upper end of the pocket.

6. The athletic pants as defined in claim 5, wherein both of the first and second locations are proximate a lower end of the pocket.

7. The athletic pants as defined in claim 1, wherein each second region has a circumference disposed orthogonally to a longitudinal axis of the pant leg; and wherein the first cinch strap does not extend around the entire circumference of the second region and therefore cannot encircle the athlete's leg when the pants are worn.

8. The athletic pants as defined in claim 3, wherein the first part of the cinch strap comprises a strip that includes one of a hook and pile fastener material thereon; and the second part of the cinch strap comprises a strap member and at least a portion of the strap member includes the other of the hook and pile fastener material; and wherein said portion of the strap member is releasably engageable with the strip, whereby a section of the second region intermediate the strip and strap member is at least partially gathered inwardly.

9. The athletic pants as defined in claim 8, wherein the strip is fixedly secured to the second region adjacent a front longitudinal edge of the pocket and the strap member is fixedly secured to the second region adjacent a rear longitudinal edge of the pocket; and wherein the strap member extends forwardly over the pocket and toward the strip.

10. The athletic pants as defined in claim 3, further comprising a second cinch strap fixedly secured to the second region of each pant leg; wherein said second cinch strap is disposed a longitudinal distance away from the first cinch strap.

11. The athletic pants as defined in claim 10, wherein the first cinch strap is disposed proximate an upper end of the pocket and the second cinch strap is disposed proximate a lower end of the pocket.

12. The athletic pants as defined in claim 1, wherein the second region of each pant leg terminates in a cuff and the cuff is adapted to be positioned proximate a mid-calf region of the athlete's leg when the pants are worn.

13. The athletic pants as defined in claim 1, wherein each pant leg further comprises a third region that extends outwardly from the second region and the third region terminates in a cuff that is adapted to be positioned proximate the athlete's ankle when the pants are worn.

14. The athletic pants as defined in claim 3, wherein the second region further defines an aperture that is positioned to align with the athlete's knee when the pants are worn; and wherein the first part of the cinch strap is disposed intermediate the pocket and the aperture.

15. The athletic pants as defined in claim 1, wherein the pants are ice hockey pants and the first region further includes a plurality of strips of hook and pile fasteners adapted to engage and secure an upper end of a hockey sock drawn over the pant legs.

16. A pair of athletic pants for providing support to an athlete's knees, the pants comprising:
a waistband adapted to encircle the athlete's waist;
a body connected to the waistband and adapted to receive the athlete's abdomen and buttocks therein;
a pair of pant legs extending outwardly from the body, the pant legs each comprising:
a first region disposed proximate the body of the pants;
a second region connected to the first region and being disposed remote from the body of the pants; and wherein the second region is manufactured from an elastic fabric that is able to apply a compressive force to the athlete's knee;
a pair of pockets formed in the second region of each pant leg and positioned so as to fall on either side of the athlete's knee;
a plurality of supporting members; each supporting member being completely enclosed within one of said pockets; and
a third region connected to the second region and terminating in a cuff that is adapted to be positioned proximate the athlete's ankles when the pants are worn.

17. The athletic pants as defined in claim 16, wherein the first and third regions are manufactured from substantially the same material and the second region is manufactured from a different material to that of first and second regions, and said different material is of a type that is able to apply a compressive force to the athlete's knee region when the pants are worn.

18. A pair of athletic pants for providing support to an athlete's knees, the pants comprising:
a waistband adapted to encircle the athlete's waist;
a body connected to the waistband and adapted to receive the athlete's abdomen and buttocks therein;
a pair of pant legs extending outwardly from the body, the pant legs each comprising:
a first region disposed proximate the body of the pants;
a second region connected to the first region and being disposed remote from the body of the pants; and wherein the second region is manufactured from an elastic fabric that is able to apply a compressive force to the athlete's knee;
a pair of pockets formed in the second region of each pant leg and positioned so as to fall on either side of the athlete's knee;
a plurality of supporting members; each supporting member being completely enclosed within one of said pockets; and
a third region connected to the second region and terminating in a cuff that is adapted to be positioned proximate the athlete's ankles when the pants are worn; and wherein the first and third regions are manufactured from substantially the same material and the second region is manufactured from a different material to that of first and second regions, and said different material is of a type that is able to apply a compressive force to the athlete's knee region when the pants are worn; and
a pair of cinch straps provided on the second region of each pant leg, said cinch straps being disposed longitudinally a spaced distance away from each other; and wherein said cinch straps are operable to tighten the pants in the athlete's knee area.

19. The athletic pants as defined in claim 18, wherein the cinch straps each comprise:
a first part that is fixedly secured to the second region in a first location;
a second part that is fixedly secured to the second region in a second location that is remote from the first location, and wherein one of said first and second parts of each cinch strap is releasably engageable with the other of the first and second parts.

20. The athletic pants as defined in claim 19, wherein the first part of each cinch strap comprises a strip that includes one of a hook and pile fastener material thereon; and
the second part of each cinch strap comprises a strap member and at least a portion of said strap member includes the other of the hook and pile fastener material; and wherein said portion of the strap member is releasably engageable with the strip, whereby a section of the second region intermediate the strip and strap member is at least partially gathered inwardly.

21. The pair of athletic pants as defined in claim 1, further comprising:

a reinforced area disposed in a front of the second region of each pant leg and intermediate the pockets, said reinforced area being adapted to be disposed adjacent the athlete's knee.

22. The pair of athletic pants as defined in claim 21, further comprising:
an aperture defined in the front of the second region of each pant leg and adjacent the reinforced area, said aperture being adapted to be disposed adjacent the patella on the athlete's knee.

23. A pair of athletic pants for providing support to an athlete's knees, the pants comprising:
a waistband adapted to encircle the athlete's waist;
a body connected to the waistband and adapted to receive the athlete's abdomen and buttocks therein;
a pair of pant legs extending outwardly from the body, the pant legs including:
a resilient fabric provided in a region of each of the pant legs that will be disposed adjacent the athlete's knee;
a pair of pockets formed in the region of each pant leg and positioned so as to fall on either side of the athlete's knee;
a plurality of supporting members; each supporting member being completely enclosed within one of said pockets; and
at least one first cinch strap provided on the region of each pant leg, said first cinch strap being operable to reduce the diameter of the pant leg in an area proximate the athlete's knee, thereby adjusting the fit of the pant for the athlete.

24. The pair of athletic pants as defined in claim 23, further comprising:
a reinforced area disposed in a front of the resilient fabric of each pant leg and intermediate the pockets, said reinforced area being adapted to be disposed adjacent the athlete's knee.

25. The pair of athletic pants as defined in claim 24, further comprising:
an aperture defined in the front of each pant leg and adjacent the reinforced area, said aperture being adapted to be disposed adjacent the patella on the athlete's knee.

26. The pair of athletic pants as defined in claim 16, further comprising:
a reinforced area disposed in a front of the second region of each pant leg and intermediate the pockets, said reinforced area being adapted to be disposed adjacent the athlete's knee.

27. The pair of athletic pants as defined in claim 26, further comprising:
an aperture defined in the front of the second region of each pant leg and adjacent the reinforced area, said aperture being adapted to be disposed adjacent the patella on the athlete's knee.

28. A pair of athletic pants for providing support to an athlete's knees, the pants comprising:
a waistband adapted to encircle the athlete's waist;
a body connected to the waistband and adapted to receive the athlete's abdomen and buttocks therein;
a pair of pant legs extending outwardly from the body, the pant legs including:
a resilient fabric provided in a region of each of the pant legs that will be disposed adjacent the athlete's knee; said fabric applying a compressive force to the athlete's knee;
a pair of pockets formed in the region of each pant leg and positioned so as to fall on either side of the athlete's knee; and
a plurality of supporting members; each supporting member being completely enclosed within one of said pockets.

29. The pair of athletic pants as defined in claim 28, further comprising:
a reinforced area provided in a front of the region of each pant leg intermediate the pockets, said reinforced area being adapted to be disposed adjacent the athlete's knee.

30. The pair of athletic pants as defined in claim 29, further comprising:
an aperture defined in the front of each pant leg and adjacent the reinforced area, said aperture being adapted to be disposed adjacent the patella on the athlete's knee.

* * * * *